United States Patent
Moriyuki

(10) Patent No.: US 10,444,302 B2
(45) Date of Patent: Oct. 15, 2019

(54) FOREIGN MATTER DETECTING DEVICE AND LINEAR GUIDE

(71) Applicant: THK CO., LTD., Tokyo (JP)

(72) Inventor: Yoshinobu Moriyuki, Tokyo (JP)

(73) Assignee: THK CO., LTD., Tokyo (JP)

( * ) Notice: Subject to any disclaimer, the term of this patent is extended or adjusted under 35 U.S.C. 154(b) by 0 days.

(21) Appl. No.: 16/328,958

(22) PCT Filed: Aug. 25, 2017

(86) PCT No.: PCT/JP2017/030595
§ 371 (c)(1),
(2) Date: Feb. 27, 2019

(87) PCT Pub. No.: WO2018/043353
PCT Pub. Date: Mar. 8, 2018

(65) Prior Publication Data
US 2019/0242953 A1      Aug. 8, 2019

(30) Foreign Application Priority Data
Sep. 2, 2016    (JP) .................................. 2016-172098

(51) Int. Cl.
*G01R 33/07* (2006.01)
*G01R 33/038* (2006.01)
(Continued)

(52) U.S. Cl.
CPC .......... *G01R 33/07* (2013.01); *G01R 33/0011* (2013.01); *G01R 33/038* (2013.01); *G01V 3/105* (2013.01)

(58) Field of Classification Search
CPC ... G01R 33/07; G01R 33/0011; G01R 33/038
USPC ...................................................... 324/207.2
See application file for complete search history.

(56) References Cited

U.S. PATENT DOCUMENTS

| 9,581,204 B2 * | 2/2017 | Yoshida .............. F16C 29/0602 |
| 2001/0016089 A1 * | 8/2001 | Mochizuki .............. B23Q 1/58 384/45 |

(Continued)

FOREIGN PATENT DOCUMENTS

| JP | 62-276454 A | 12/1987 |
| JP | 2-138518 A | 5/1990 |

(Continued)

OTHER PUBLICATIONS

International Search Report dated Oct. 10, 2017, issued in counterpart International Application No. PCT/JP2017/030595, with English Translation. (4 pages).

(Continued)

*Primary Examiner* — Reena Aurora
(74) *Attorney, Agent, or Firm* — Westerman, Hattori, Daniels & Adrian, LLP

(57) ABSTRACT

A foreign matter detecting device comprises a first yoke portion and a second yoke portion which adjoin a permanent magnet respectively. The both yoke portions are arranged while interposing a reference space therebetween. Further, a detour yoke portion is arranged. A magnetic resistance of the first detour space being smaller than a magnetic resistance of the predetermined reference space, and magnetic resistances of the second detour space and the first detour space being larger than the magnetic resistance of the predetermined reference space. A detection signal in relation to the foreign matter is outputted on the basis of a magnetic flux density provided in at least any one of spaces of the reference space and the first detour space, corresponding to an amount of retention of the foreign matter in a retaining portion which is provided so that the foreign matter is retained in the second detour space.

7 Claims, 7 Drawing Sheets

(51) Int. Cl.
    *G01R 33/00*     (2006.01)
    *G01V 3/10*     (2006.01)

(56)     References Cited

U.S. PATENT DOCUMENTS

| | | | |
|---|---|---|---|
| 2009/0091312 A1* | 4/2009 | Ito | G01D 5/147 324/207.2 |
| 2012/0126796 A1* | 5/2012 | Drespling | G01D 5/145 324/207.2 |
| 2016/0215825 A1 | 7/2016 | Yoshida et al. | |

FOREIGN PATENT DOCUMENTS

| | | |
|---|---|---|
| JP | 8-338220 A | 12/1996 |
| JP | 2000-74615 A | 3/2000 |
| JP | 2003-80107 A | 3/2003 |
| JP | 2009-92204 A | 4/2009 |
| JP | 2014-224811 A | 12/2014 |
| JP | 2015-34743 A | 2/2015 |
| JP | 2015-52362 A | 3/2015 |
| JP | 2015-210235 A | 11/2015 |

OTHER PUBLICATIONS

Decision to Grant a Patent dated Jun. 5, 2018, issued in counterpart of Japanese Patent Application No. 2016-172098 with English Translation (5 pages).

Notification of Reasons for Refusal dated Mar. 6, 2018, issued in counterpart of Japanese Patent Application No. 2016-172098 with English Translation (6 pages).

* cited by examiner

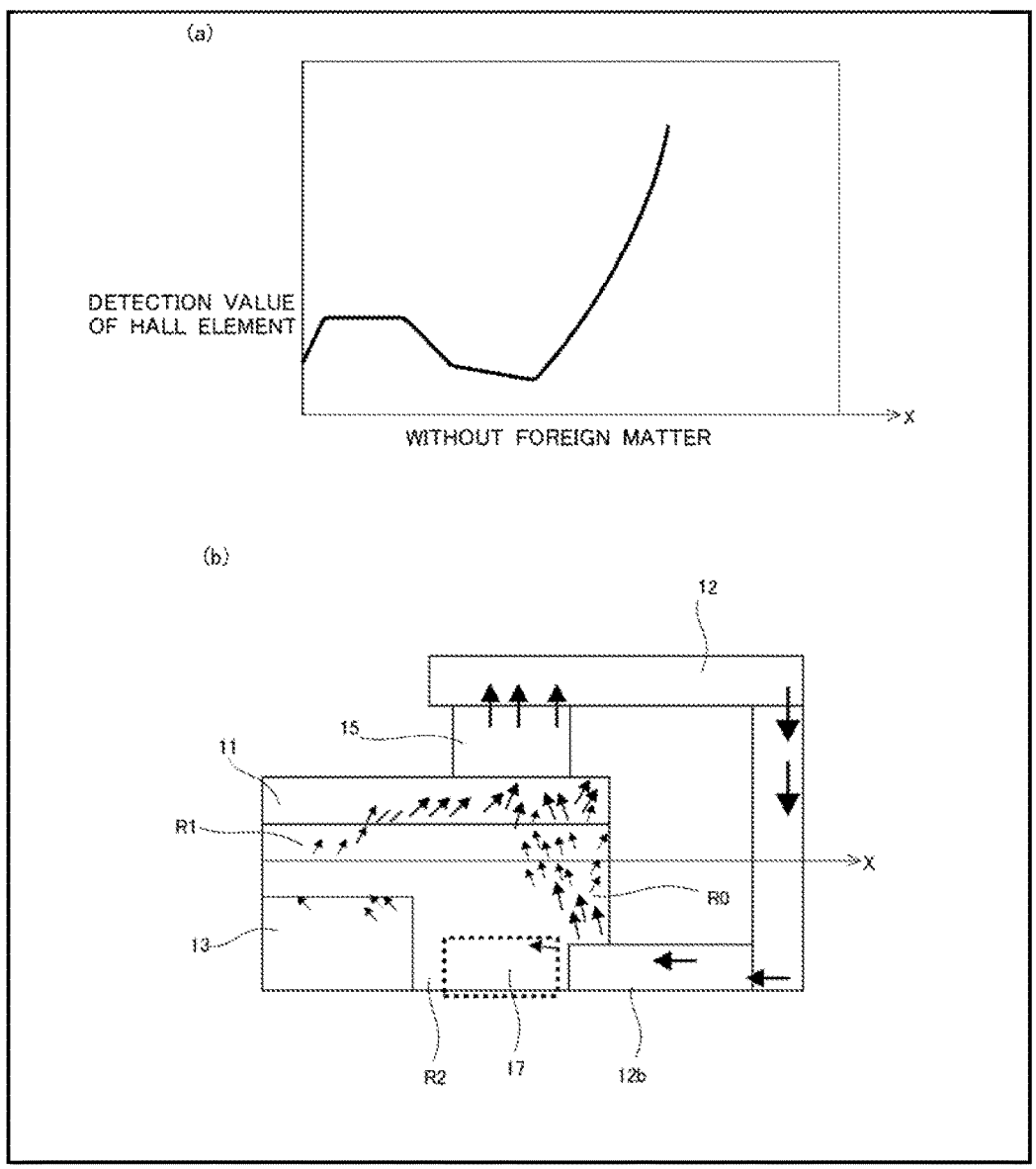

FOREIGN MATTER DETECTING DEVICE AND LINEAR GUIDE

TECHNICAL FIELD

The present invention relates to a device for detecting a foreign matter including a magnetic material, and a linear guide provided with the device.

BACKGROUND ART

When a linear guide, which is a direct acting apparatus, is driven, then the exfoliation occurs on a track surface and/or a surface (sliding surface) of a rolling member, and the linear guide is exposed to the exfoliated matter or the like. If the linear guide is exposed to the foreign matter such as the exfoliated matter or the like brought about as described above, then the foreign matter enters the track surface and/or the sliding surface, and problems arise such that the vibration becomes conspicuous upon the direct acting and/or the service life of the linear guide is shortened. In view of the above, for example, Patent Literature 1 discloses a technique concerning a direct acting apparatus provided with a detecting device for detecting a metal foreign matter. In the case of this technique, a pair of electrodes are arranged at a portion at which the foreign matter is easily accumulated in the direct acting apparatus. When the foreign matter is progressively accumulated at the portion, then a short circuit is electrically formed between the electrodes on account of the conductivity of the foreign matter, and the presence of the foreign matter is consequently detected.

Further, if the foreign matter includes the magnetic material such as iron or the like, the foreign matter can be detected by utilizing the magnetic force (magnetic flux density) of a permanent magnet as well. For example, when the magnetic flux density, which is provided in a predetermined magnetic circuit, is detected by utilizing a Hall element, if the foreign matter, which includes the magnetic material, invades a part of the structure of the magnetic circuit, then the magnetic flux, which comes from the permanent magnet, arrives at the Hall element in series while passing through the foreign matter existing in the magnetic circuit. As a result, the magnetic flux density, which is detected by the Hall element, changes. Therefore, the invasion of the foreign matter into the magnetic circuit is detected on the basis of the change.

PRIOR ART LITERATURE

Patent Literature

Patent Literature 1: Japanese Patent Application Laid-Open No. 2009-92204

SUMMARY OF THE INVENTION

Problems to be Solved by the Invention

The structure, in which the foreign matter is detected by utilizing the magnetic force of the permanent magnet, does not use the electric power directly for detecting the foreign matter. Therefore, the structure is useful in an environment in which the use of the electric power is restricted, including, for example, the interior of a machine tool in which a coolant is used. However, when the magnetic circuit, which is provided to detect the foreign matter while ranging from the permanent magnet to the Hall element, is configured in series as in the conventional technique, even if the foreign matter enters the magnetic circuit, then the amount of the foreign matter as the detection target is not so large in general. As a result, the amount of change of the magnetic flux density detected by the Hall element is not large. Therefore, in the case of the conventional technique, it is difficult to raise the accuracy of the detection of the foreign matter.

Further, when the foreign matter is detected with an apparatus such as a linear guide or the like which performs the direct acting operation, it is preferable that the detection can be performed for a smaller amount of the foreign matter in order to preferably maintain the operation environment of the apparatus. However, the smaller the amount of the foreign matter as the detection target is, the smaller the amount of change of the magnetic flux density detected by the Hall element in the conventional technique is. Therefore, it is not easy to detect a small amount of the foreign matter highly accurately.

The present invention has been made taking the foregoing problems into consideration, an object of which is to provide a foreign matter detecting device which makes it possible to highly accurately detect a foreign matter including a magnetic material at the stage where the amount of the foreign matter is as small as possible.

Means for Solving the Problems

In the present invention, in order to solve the problems as described above, a magnetic circuit is constructed so that the flow of the magnetic flux in the magnetic circuit is greatly changed if a foreign matter, which includes a magnetic material, exists at a part for forming the magnetic circuit of a foreign matter detecting device. The presence of the foreign matter can be detected highly accurately at the stage where the amount of the foreign matter is as small as possible, by capturing the change in the magnetic flux density which is as large as possible and which is generated in accordance with the change in the flow of the magnetic flux in the magnetic circuit as described above.

In particular, the present invention resides in a foreign matter detecting device for detecting a predetermined foreign matter including a magnetic material; the foreign matter detecting device comprising a permanent magnet; a first yoke portion which is arranged while adjoining the permanent magnet; a second yoke portion which adjoins the permanent magnet at a region different from that of the first yoke portion, the second yoke portion being arranged separately at a second yoke predetermined region different from the adjoining region while interposing a predetermined reference space with respect to the first yoke portion; a detour yoke portion which is arranged separately while interposing a first detour space different from the predetermined reference space, with respect to the first yoke portion and which is arranged separately while interposing a second detour space with respect to the second yoke predetermined region of the second yoke portion, a magnetic resistance of the first detour space being smaller than a magnetic resistance of the predetermined reference space, and magnetic resistances of the second detour space and the first detour space being larger than the magnetic resistance of the predetermined reference space; a retaining portion which is provided so that the predetermined foreign matter can enter the retaining portion via an opening portion provided on an outer surface of a device body and the entered predetermined foreign matter is retained in the second detour space; and a detecting portion which outputs a detection signal in relation to the predetermined foreign matter on the basis of a magnetic flux density provided in at least any one of spaces of the predetermined reference space and the first detour space, corresponding to an amount of retention of the predetermined foreign matter in the retaining portion.

In the foreign matter detecting device according to the present invention, the magnetic circuit is formed to detect the predetermined foreign matter by the permanent magnet, the first yoke portion, the second yoke portion, the detour yoke portion, and the spaces between the respective yoke portions. Further, the magnetic circuit includes a reference magnetic circuit which is formed by the permanent magnet, the first yoke portion, the second yoke portion, and the predetermined reference space and a detour magnetic circuit which is formed by the permanent magnet, the first yoke portion, the second yoke portion, the detour yoke portion, and the first and second detour spaces.

In this case, the reference magnetic circuit includes the first yoke portion and the second yoke portion which are arranged while interposing the predetermined reference space. In this context, the second yoke predetermined region of the second yoke portion is the region which is approximately opposed to the first yoke portion while interposing the predetermined reference space. On the other hand, the detour magnetic circuit includes the detour yoke portion. Thus, the second yoke predetermined region of the second yoke portion is approximately opposed to the detour yoke portion while interposing the second detour space, and the detour yoke portion is also opposed to the first yoke portion while interposing the first detour space. That is, in the foreign matter detecting device according to the present invention, the magnetic circuit, through which the magnetic flux coming from the permanent magnet flows, includes a sub-circuit (sub-circuit disposed on a side of the reference magnetic circuit) in which the magnetic flux flows from the second yoke predetermined region of the second yoke portion to the first yoke portion and a sub-circuit (sub-circuit disposed on a side of the detour magnetic circuit) in which the magnetic flux flows from the second yoke predetermined region via the detour yoke portion to the first yoke portion. The both sub-circuits exist in parallel to one another.

In this case, the predetermined reference space is included in the sub-circuit disposed on the side of the reference magnetic circuit, and the first detour space and the second detour space are included in the sub-circuit disposed on the side of the detour magnetic circuit. Then, the magnetic resistance of the first detour space is set to be smaller than the magnetic resistance of the predetermined reference space. Further, the sum of the magnetic resistances of the second detour space and the first detour space is set to be larger than the magnetic resistance of the predetermined reference space. Note that the magnetic resistance of each of the spaces can be adjusted by the aid of various physical parameters relevant to the magnetic resistance. As the physical parameter, it is possible to exemplify, for example, the spacing distance between the respective yoke portions, the cross-sectional area of each of the yoke portions, and the overlapping area between the yoke portions. Further, the retaining portion, in which the foreign matter having entered the foreign matter detecting device from the outside thereof is retained, is formed in the second detour space. When the foreign matter, which is retained in the retaining portion, includes the magnetic material, the magnetic resistance in relation to the second detour space is lowered on account of the retention of the foreign matter in the retaining portion.

In the foreign matter detecting device having the magnetic circuits formed as described above, when the foreign matter is not retained in the retaining portion, or when the amount of retention is small, then most of the magnetic flux coming from the permanent magnet easily flows through the sub-circuit disposed on the side of the reference magnetic circuit via the second yoke predetermined region of the second yoke portion, owing to the fact that the magnetic resistance of the predetermined reference space is smaller than the sum of the magnetic resistances of the first detour space and the second detour space, in other words, owing to the fact that the magnetic resistance, which is provided in the sub-circuit disposed on the side of the reference magnetic circuit, is smaller than the magnetic resistance which is provided in the sub-circuit disposed on the side of the detour magnetic circuit. As a result, the magnetic flux, which flows through the sub-circuit disposed on the side of the detour magnetic circuit via the second yoke predetermined region of the second yoke portion, is decreased.

Then, when the foreign matter enters the retaining portion, and the amount of retention thereof is progressively increased, then the magnetic resistance of the second detour space is progressively lowered magnetically. Ideally, on account of the retention of the foreign matter in the second detour space, the magnetic resistance of the second detour space is lowered to the magnetic resistance which is the same as or equivalent to those of the respective yoke portions. If the magnetic resistance of the second detour space is progressively lowered on account of the retention of the foreign matter in the retaining portion as described above, the magnetic resistance, which is provided in the sub-circuit disposed on the side of the reference magnetic circuit, becomes larger than the magnetic resistance which is provided in the sub-circuit disposed on the side of the detour magnetic circuit. As a result, most of the magnetic flux coming from the permanent magnet flows through the sub-circuit disposed on the side of the detour magnetic circuit via the second yoke predetermined region of the second yoke portion. The magnetic flux, which flows through the sub-circuit disposed on the side of the reference magnetic circuit via the second yoke predetermined region of the second yoke portion, is decreased.

That is, in the foreign matter detecting device according to the present invention, the situation changes or switches between the situation in which most of the magnetic flux coming from the second yoke predetermined region of the second yoke portion flows through the predetermined reference space and the situation in which most of the magnetic flux flows through the first detour space, depending on the amount of retention of the foreign matter in the retaining portion. In this case, the circuit itself, through which the magnetic flux coming from the permanent magnet flows, switches depending on the amount of retention of the foreign matter. Therefore, the magnetic flux density greatly changes in the predetermined reference space and the first detour space. Accordingly, the detecting portion can highly accurately output the detection signal in relation to the retained foreign matter, on the basis of the magnetic flux density in at least any one of the spaces of the predetermined reference space and the first detour space, corresponding to the amount of retention of the foreign matter in the retaining portion. Further, if the foreign matter is retained in the retaining portion to such an extent that the magnetic resistance of the second detour space is sufficiently lowered, it is possible to output the highly accurate detection signal as described above. Therefore, it is possible to suppress the amount of the foreign matter required for the detection of the foreign matter so that the amount of the foreign matter is as small as possible.

Advantageous Effect of the Invention

It is possible to provide the foreign matter detecting device which makes it possible to highly accurately detect the foreign matter including the magnetic material at the stage where the amount of the foreign matter is as small as possible.

BRIEF DESCRIPTION OF THE DRAWINGS

FIG. 5 shows a magnetic flux distribution in the magnetic circuit formed in the foreign matter detecting device when no foreign matter exists in the foreign matter detecting device shown in FIG. 3.

EMBODIMENTS FOR CARRYING OUT THE INVENTION

An explanation will be made below on the basis of the drawings about a specified embodiment of the present invention. For example, the dimension or size, the material, the shape, and the relative arrangement of constitutive parts or components described in the embodiments of the present invention are not intended to limit the technical scope of the invention only thereto unless specifically noted.

First Embodiment

Figure 1:
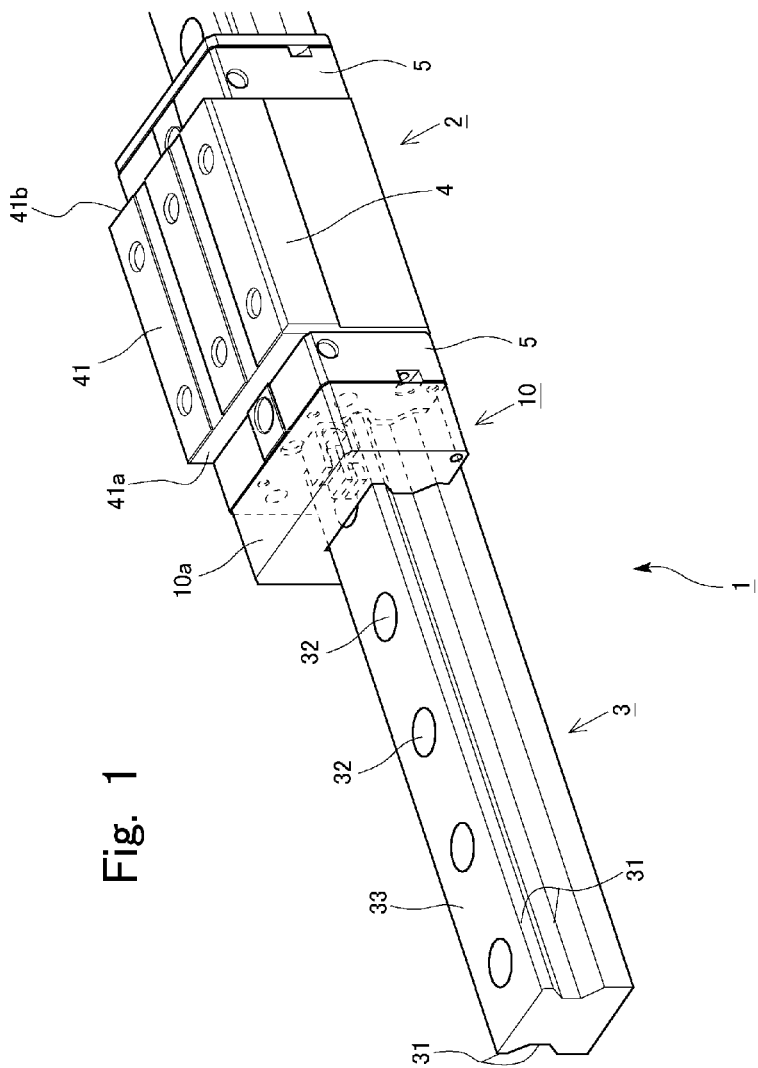
FIG. 1 shows a first drawing illustrating a schematic arrangement of a linear guide provided with a foreign matter detecting device according to the present invention.

FIG. 1 shows a perspective view illustrating an embodiment of a linear guide 1 as one of rolling guide apparatuses to which a foreign matter detecting device 10 according to the present invention is applied. The linear guide 1 is composed of a track rail 3 as a track member which is formed to have a straight shape, and a movable block 2 as a movable member which is assembled in a channel form to the track rail 3 by the aid of a plurality of balls as a plurality of rolling members and which has an endless circulating passage for the balls provided therein. The balls circulate in the endless circulating passage of the movable block 2, and thus the movable block 2 relatively moves in the longitudinal direction on the track rail 3.

The track rail 3 is formed to have a substantially rectangular shape in cross section. Further, bolt attachment holes 32 are formed in the direction directed from an upper surface 33 to a lower surface of the track rail 3 at predetermined intervals along with a central axis in the longitudinal direction of the upper surface 33. Fixing bolts made of steel are fastened to the bolt attachment holes 32, and thus the track rail 3 can be fixed to a fixed member such as a bed, a column or the like. Further, two stripes of ball rolling surfaces 31, on which the balls roll, are formed in the longitudinal direction on each of left and right side surfaces of the track rail 3 which do not interfere with the bolt attachment holes 32. Four stripes of ball rolling surfaces 31 in total are formed on the track rail 3. Note that the four stripes of ball rolling surfaces 31 are formed on the track rail 3 according to the present invention, but the setting of the number of stripes and the arrangement of the ball rolling surfaces 31 can be appropriately changed depending on the way of use of the linear guide 1 and the magnitude of the load to be loaded.

Further, the movable block 2 is composed of a main block body 4 which has an attachment surface 41 for fixing a movable member such as a table or the like thereto, and end plates 5 as a pair of cover members which are installed respectively to both end portions 41a, 41b in the relative movement direction of the main block body 4. Note that an unillustrated seal member is installed to the end plate 5. The seal member hermetically seals the gap between the end plate 5 and the upper surface 33 of the track rail 3, and the seal member prevents the foreign matter such as dust or the like adhered to the track rail 3 from entering the inside of the movable block 2. Further, when the linear guide 1 is utilized, for example, at the inside of a machine tool, the track rail 3 is exposed in some cases to a coolant including sawdust of iron pieces or scraps or the like. The seal member avoids such a situation that the sawdust or the like as described above enters, as the foreign matter, the inside of the movable block 2.

In this context, as described above, the linear guide 1 is constructed so that the invasion of the foreign matter into the inside of the movable block 2 is inhibited by the seal member provided for the end plate 5. However, it is not easy to stop the invasion of all of the foreign matter by means of the sealing ability of the seal member. Further, if the linear guide 1 is placed in an environment in which the linear guide 1 is exposed to the foreign matter for a long period of time, the foreign matter easily enters the inside of the movable block 2, for example, due to the aged deterioration of the seal member. If the foreign matter enters the inside of the movable block 2, the direct acting operation thereof may be affected thereby. On this account, it is preferable to detect the fact that the movable block 2 is in a state of being exposed to the foreign matter to some extent so that the user is informed of the maintenance of the linear guide 1, before the influence of the foreign matter becomes apparent. Accordingly, the foreign matter detecting device 10 is attached to the linear guide 1 on the outer side of the end plate 5 which is included in the end plates 5 provided at the end portions on the both sides of the main block body 4 and which is provided on the side of the end portion 41a.

Figure 2:
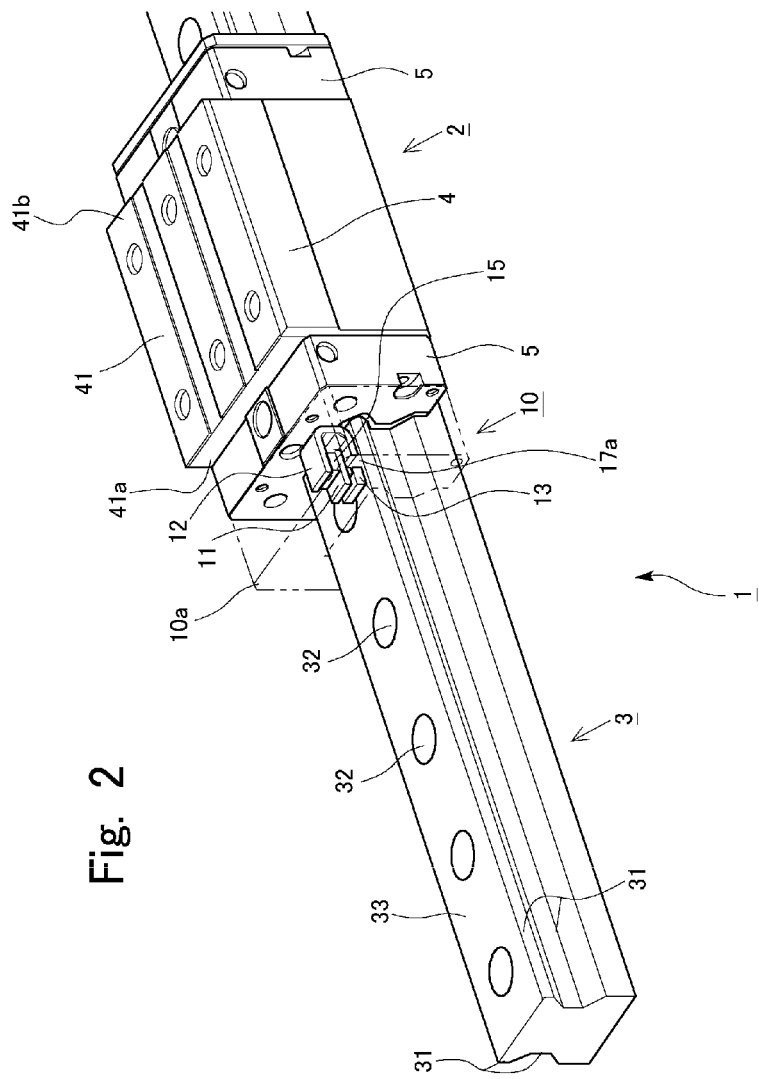
FIG. 2 shows a second drawing illustrating the schematic arrangement of the linear guide provided with the foreign matter detecting device according to the present invention.
Figure 3:
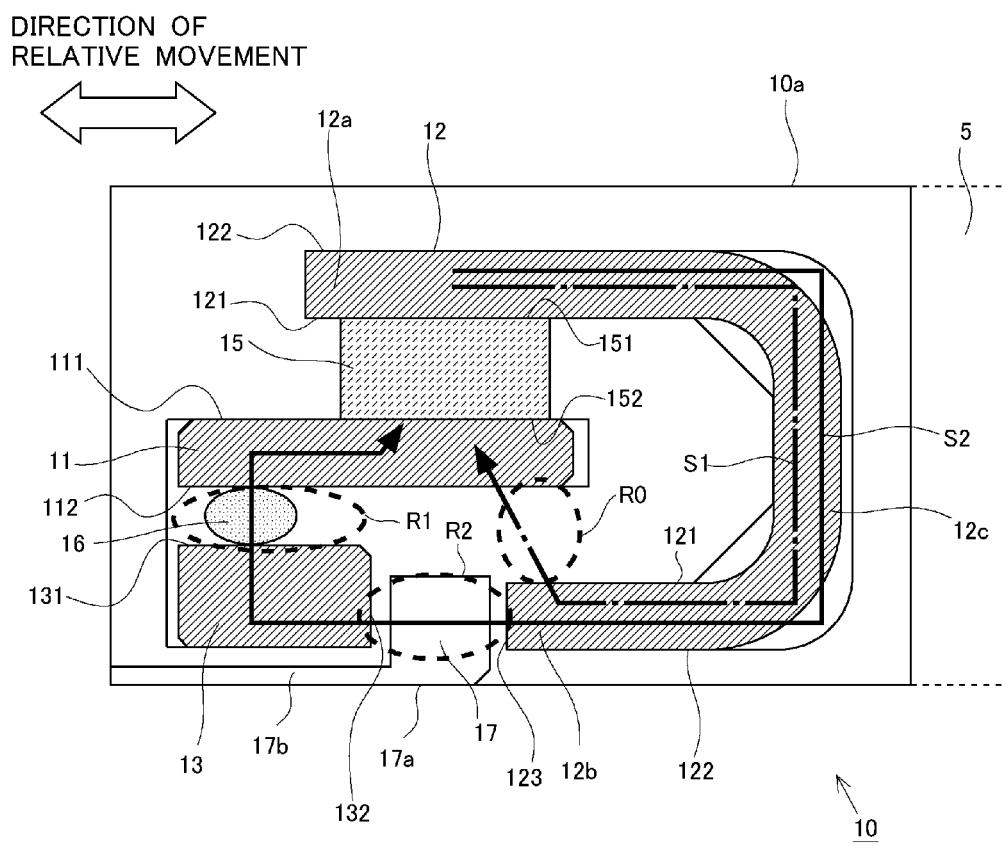
FIG. 3 shows a schematic arrangement of the foreign matter detecting device according to the present invention.

The foreign matter detecting device 10 is the device which makes it possible to detect the foreign matter including the magnetic material such as iron or the like by using the magnetic circuit formed by utilizing the magnetic flux coming from the permanent magnet 15 at the inside of a device body 10a. Note that FIG. 2 is a transparent view in which the device body 10a is omitted from the illustration in order to visualize the main constitutive components for forming the magnetic circuit provided at the inside of the foreign matter detecting device 10. Further, FIG. 3 shows a sectional view of the foreign matter detecting device 10, taken in the direction of the relative movement of the movable block 2 (in the longitudinal direction of the track rail 3). Therefore, FIG. 3 shows a cross section as obtained when the foreign matter detecting device 10 is viewed from a side position concerning the linear guide 1. In FIG. 3, the end plate 5, to which the foreign matter detecting device 10 is attached, exists on the right side of the foreign matter detecting device 10. In FIG. 3, the lower portion of the device body 10a of the foreign matter detecting device 10 is in a state of being opposed to the upper surface 33 of the track rail 3 in a state of being attached to the end plate 5.

An explanation will now be made about the detailed structure of the foreign matter detecting device 10. The foreign matter detecting device 10 has the permanent magnet 15, a first yoke portion 11, a second yoke portion 12, and a detour yoke portion 13 which are provided in the device body 10a as the constitutive components for forming the magnetic circuit as described above. The permanent magnet 15 functions as a supply source for supplying the magnetic flux in order to detect the foreign matter including the magnetic material. In this embodiment, the permanent magnet 15 is formed to have a rectangular shape. The permanent magnet 15 and the first yoke portion 11 are arranged in the device body 10a in a state in which the both are brought in contact with each other and the both are adjacent to one another so that a surface 152, which is one surface thereof, is completely covered with the first yoke portion 11. Further, as for the permanent magnet 15, the permanent magnet 15 and the second yoke portion 12 are arranged in the device body 10a in a state in which the both are brought in contact with each other and the both are adjacent to one another so that a surface 151, which is disposed on a side opposite to the surface 152 covered with the first yoke portion 11, is completely covered with the second yoke portion 12.

Then, the first yoke portion 11 is a plate-shaped yoke member having a constant thickness (dimension or size in the upward-downward direction as viewed in FIG. 3). As for the plate-shaped first yoke portion 11, one surface 111 thereof covers the surface 152 of the permanent magnet 15 as described above, and the other surface 112 is opposed to an end portion 12b of the second yoke portion 12 and the detour yoke portion 13 as described later on. Note that the relative positional relationship of the respective members and details of the dimension will be described later on.

In the next place, the second yoke portion 12 has the same constant thickness as that of the first yoke portion 11. The second yoke portion 12 has a shape curved in a U-shaped form in the cross section shown in FIG. 3. In the U-shaped form, the inner surface is referred to by reference numeral 121, and the outer surface is referred to by reference numeral 122. Therefore, the surface 121 of the second yoke portion 12 is brought in contact with the surface 151 of the permanent magnet 15. More specifically, as for the second yoke portion 12, the inner surface 121 is brought in contact with the surface 151 of the permanent magnet 15 at one end portion 12a in the cross section, and the inner surface 121 covers the surface 151. Then, the second yoke portion 12 extends by a predetermined length from the end portion 12a toward the end plate 5. Further, the second yoke portion 12 curves and extends in the downward direction of the device body 10a, and thus a straight portion 12c is formed. The length of the straight portion 12c is such a length that the end on the downward side is positioned further downwardly as compared with the first yoke portion 11 in the cross section shown in FIG. 3. Further, the second yoke portion 12 curves and extends from the end of the straight portion 12c in the direction to make separation from the end plate 5, i.e., in the direction directed to the first yoke portion 11, and thus the second yoke portion 12 finally arrives at the other end portion 12b of the second yoke portion 12. Note that the end portion 12b corresponds to the second yoke predetermined portion according to the present invention. At the end portion 12b, the inner surface 121 of the second yoke portion 12 is allowed to be in a positional relationship opposed to the surface 112 of the first yoke portion 11. In other words, at the end portion 12b of the second yoke portion 12, the surface 121 is allowed to be in a positional relationship separated while interposing the reference space R0 with respect to the surface 112 of the first yoke portion 11.

In the next place, the detour yoke portion 13 has an approximately rectangular parallelepiped shape. In the cross section shown in FIG. 3, the surface 131 of the detour yoke portion 13 is allowed to be in a positional relationship opposed to the surface 112 of the first yoke portion 11. In other words, the surface 131 of the detour yoke portion 13 is allowed to be in a positional relationship separated while interposing the first detour space R1 with respect to the surface 112 of the first yoke portion 11. Note that the opposing position, at which the detour yoke portion 13 is opposed to the surface 112 of the first yoke portion 11, is different from the opposing position at which the end portion 12b of the second yoke portion 12 is opposed to the surface 112. Further, in the cross section shown in FIG. 3, the surface 132, which adjoins the surface 131 of the detour yoke portion 13 and which has the direction that differs by approximately 90 degrees, is allowed to be in a positional relationship opposed to the end surface 123 of the end portion 12b of the second yoke portion 12. In other words, the surface 132 of the detour yoke portion 13 is allowed to be in a positional relationship separated while interposing the second detour space R2 with respect to the end surface 123 of the end portion 12b of the second yoke portion 12.

Further, a Hall element 16, which can detect the magnetic flux density, is arranged in the first detour space R1 between the first yoke portion 11 and the detour yoke portion 13. The Hall element 16 corresponds to the sensor element of the present invention. The output thereof is sent to an unillustrated detection circuit, and a detection signal is generated corresponding to the detected magnetic flux density. In this way, the detecting portion of the present invention is formed by the Hall element 16 and the detection circuit corresponding thereto. Note that any device, which can detect the magnetic flux density, can be adopted as the sensor element of the present invention in place of the Hall element 16. Further, a retaining portion 17, which is a recess having a volume capable of retaining a predetermined amount of the foreign matter, is formed in the second detour space R2 between the second yoke portion 12 and the detour yoke portion 13 so that the retaining portion 17 occupies almost all of the second detour space R2. The retaining portion 17 has an opening portion 17a which is open in the downward direction of the device body 10a. In a state of the linear guide 1 in which the foreign matter detecting device 10 is attached to the end plate 5, the opening portion 17a is in a state of being open toward the upper surface 33 of the track rail 3. Therefore, the foreign matter, which exists on the upper surface 33, can enter the inside of the retaining portion 17 via the opening portion 17a. Further, an intake groove 17b, which extends in the direction of relative movement of the movable block 2 and which is linked to the opening portion 17a of the retaining portion 17, is formed on the outer surface disposed at the lower portion of the device body 10a. According to the configuration as described above, when the movable block 2 is moved to the left as viewed in FIG. 3 on the track rail 3 (when the movable block 2 is moved leftwardly in the downward direction as viewed in FIG. 2), then the foreign matter, which exists on the upper surface 33 of the track rail 3, easily enters the retaining portion 17 via the intake groove 17b and the opening portion 17a, and the foreign matter is easily retained. Note that the retaining portion 17 is positioned approximately on the lower side of the permanent magnet 15. Therefore, the magnetic force of the permanent magnet 15 easily acts in the retaining portion 17. As a result, the foreign matter (foreign matter including the magnetic material), which has entered the retaining portion 17, is easily retained in the retaining portion 17 by means of the magnetic force. The foreign matter, which has once entered the retaining portion 17, is hardly disengaged from the opening portion 17a again.

In this context, in the foreign matter detecting device 10, two magnetic circuits are formed, which are indicated by an alternate long and short dash line arrow and a solid line arrow as shown in FIG. 3. Specifically, the former magnetic circuit S1 is formed to extend along the permanent magnet 15, the second yoke portion 12, the reference space R0, and the first yoke portion 11, and the former magnetic circuit S1 is referred to as "reference magnetic circuit S1." Further, the latter magnetic circuit S2 is formed to extend along the permanent magnet 15, the second yoke portion 12, the second detour space R2, the detour yoke portion 13, the first detour space R1, and the first yoke portion 11, and the latter magnetic circuit S2 is referred to as "detour magnetic circuit S2". Then, the retaining portion 17 and the Hall element 16 described above are arranged on the detour magnetic circuit S2. According to this fact, the permanent magnet 15 forms the two magnetic circuits, and the permanent magnet 15 also has the function to retain the foreign matter in the retaining portion 17 as described above.

Figure 4A:
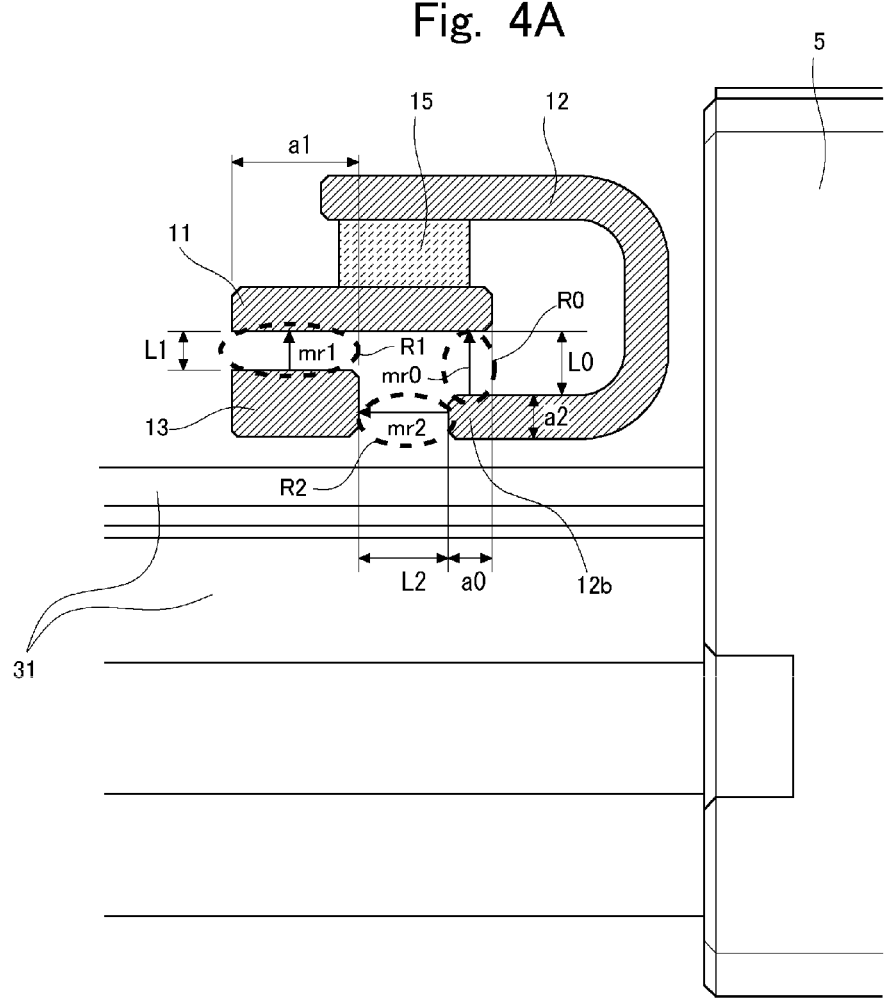
FIG. 4A shows a first drawing illustrating a relationship of arrangement of respective constitutive components for forming the magnetic circuit in the foreign matter detecting device shown in FIG. 3.
Figure 4B:
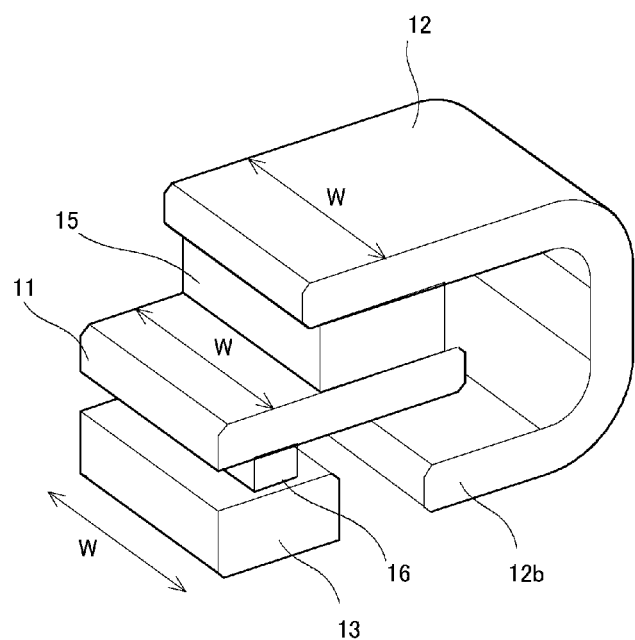
FIG. 4B shows a second drawing illustrating a relationship of arrangement of respective constitutive components for forming the magnetic circuit in the foreign matter detecting device shown in FIG. 3.

An explanation will now be made about the reference magnetic circuit S1 and the detour magnetic circuit S2 on the basis of FIGS. 4A and 4B in addition to FIG. 3. FIG. 4A schematically shows, on the same cross section as that of FIG. 3, the constitutive components of, for example, the permanent magnet 15 and the respective yoke portions for forming the magnetic circuit, and FIG. 4A shows the dimensions and the relative positional relationship of the respective constitutive components. Further, FIG. 4B shows a perspective view schematically illustrating the constitutive components of, for example, the permanent magnet 15 and the respective yoke portions for forming the magnetic circuit.

In the reference magnetic circuit S1, the magnetic resistance $mr0$ of the reference space R0, which is configured to form the circuit, is higher than the magnetic resistances of the first yoke portion 11 and the second yoke portion 12. Therefore, the flow of the magnetic flux in the reference magnetic circuit S1 is easily affected by the magnetic resistance $mr0$ of the reference space R0. Further, in the detour magnetic circuit S2, the magnetic resistance $mr1$ of the first detour space R1 and the magnetic resistance $mr2$ of the second detour space R2, which are configured to form the circuit, are higher than the magnetic resistances of the first yoke portion 11, the second yoke portion 12, and the detour yoke portion 13. Therefore, the flow of the magnetic flux in the detour magnetic circuit S2 is easily affected by the magnetic resistance $mr1$ of the first detour space R1 and the magnetic resistance $mr2$ of the second detour space R2. Accordingly, the respective magnetic circuits will be explained while the attention is given to the magnetic resistance $mr0$ of the reference space R0, the magnetic resistance $mr1$ of the first detour space R1, and the magnetic resistance $mr2$ of the second detour space R2. Note that the magnetic resistance $mr2$ is the magnetic resistance provided in a state in which the foreign matter including the magnetic material is not retained in the retaining portion 17.

As shown in FIG. 4A, as for the relative positional relationship between the first yoke portion 11 and the second yoke portion 12 which are arranged opposingly while interposing the reference space R0, the spacing distance is L0 in the upward-downward direction (i.e., the upward-downward direction of the foreign matter detecting device 10) as viewed in FIG. 4A in which the distance between the both yoke portions is the shortest, and the overlapping distance, by which the both yoke portions are overlapped with each other, is a0 in the left-right direction (i.e., the relative movement direction of the movable block 2) as viewed in FIG. 4A perpendicular to the upward-downward direction. Note that as shown in FIG. 4B, all of the widths of the first yoke portion 11, the second yoke portion 12, and the detour yoke portion 13 are the same width W. Therefore, the magnetic resistance $mr0$ of the reference space R0 fulfills the following relationship of Expression 1.

[Numerical formula 1]

$$mr0 \propto L0/(a0 \cdot W) \qquad \text{Expression 1}$$

Similarly, as for the relative positional relationship between the first yoke portion 11 and the detour yoke portion 13 which are arranged opposingly while interposing the first detour space R1, the spacing distance is L1 in the upward-downward direction as viewed in FIG. 4A in which the distance between the both yoke portions is the shortest, and the overlapping distance, by which the both yoke portions are overlapped with each other, is a1 in the left-right direction as viewed in FIG. 4A perpendicular to the upward-downward direction. Therefore, the magnetic resistance $mr1$ of the first detour space R1 fulfills the following relationship of Expression 2.

[Numerical formula 2]

$$mr1 \propto L0/(a1 \cdot W) \qquad \text{Expression 2}$$

Further, as for the relative positional relationship between the second yoke portion 12 and the detour yoke portion 13 which are arranged opposingly while interposing the second detour space R2, the spacing distance is L2 in the left-right direction as viewed in FIG. 4A in which the distance between the both yoke portions is the shortest, and the overlapping distance, by which the both yoke portions are overlapped with each other, is a2 in the upward-downward direction as viewed in FIG. 4A perpendicular to the left-right direction. Therefore, the magnetic resistance $mr2$ of the second detour space R2 fulfills the following relationship of Expression 3.

[Numerical formula 3]

$$mr2 \propto L2/(a2 \cdot W) \qquad \text{Expression 3}$$

Then, in the foreign matter detecting device 10, the following relationship represented by Expression 4 holds in relation to the magnetic resistance $mr0$ of the reference space R0, the magnetic resistance $mr1$ of the first detour space R1, and the magnetic resistance $mr2$ of the second detour space R2.

[Numerical formula 4]

$$mr1 < mr0 < mr1 + mr2 \qquad \text{Expression 4}$$

According to Expression 4, the state, in which such a relationship (relationship of $mr0 < mr1 + mr2$) holds that the magnetic resistance $mr0$ of the reference space R0 is smaller than the sum of the magnetic resistance $mr1$ of the first detour space R1 and the magnetic resistance $mr2$ of the second detour space R2, represents the relationship between the easiness of flow of the magnetic flux in the reference magnetic circuit S1 and the easiness of flow of the magnetic flux in the detour magnetic circuit S2 when the foreign matter including the magnetic material is not retained in the retaining portion 17. Therefore, when the foreign matter including the magnetic material is not retained in the retaining portion 17, such a situation is formed that the magnetic flux coming from the permanent magnet 15 easily flows through the reference magnetic circuit S1 as compared with the detour magnetic circuit S2.

On the other hand, according to Expression 4, the state, in which such a relationship holds that the magnetic resistance mr1 of the first detour space R1 is smaller than the magnetic resistance mr0 of the reference space R0 (relationship of mr1<mr0), assumes the state in which the foreign matter including the magnetic material is retained in the retaining portion 17. That is, when the foreign matter is progressively retained in the retaining portion 17, the foreign matter increasingly exists in the second detour space R2 approximately overlapped with the retaining portion 17. Therefore, when the amount of retention of the foreign matter is increased, the magnetic resistance of the second detour space R2 is lowered. Then, if the retaining portion 17 is occupied by the foreign matter, then the magnetic resistance of the second detour space R2 approaches the magnetic resistance in the second yoke portion 12 or the detour yoke portion 13, and the magnetic resistance of the second detour space R2 ideally becomes an approximately equivalent magnetic resistance. It is affirmed that the state as described above is such a state that the magnetic resistance of the second detour space R2 can be magnetically neglected on account of the retention of the foreign matter in the retaining portion 17. If the relationship, in which the magnetic resistance mr1 of the first detour space R1 is smaller than the magnetic resistance mr0 of the reference space R0, holds in the state as described above, such a situation is formed that the magnetic flux coming from the permanent magnet 15 easily flows through the detour magnetic circuit S2 as compared with the reference magnetic circuit S1.

Figure 6:
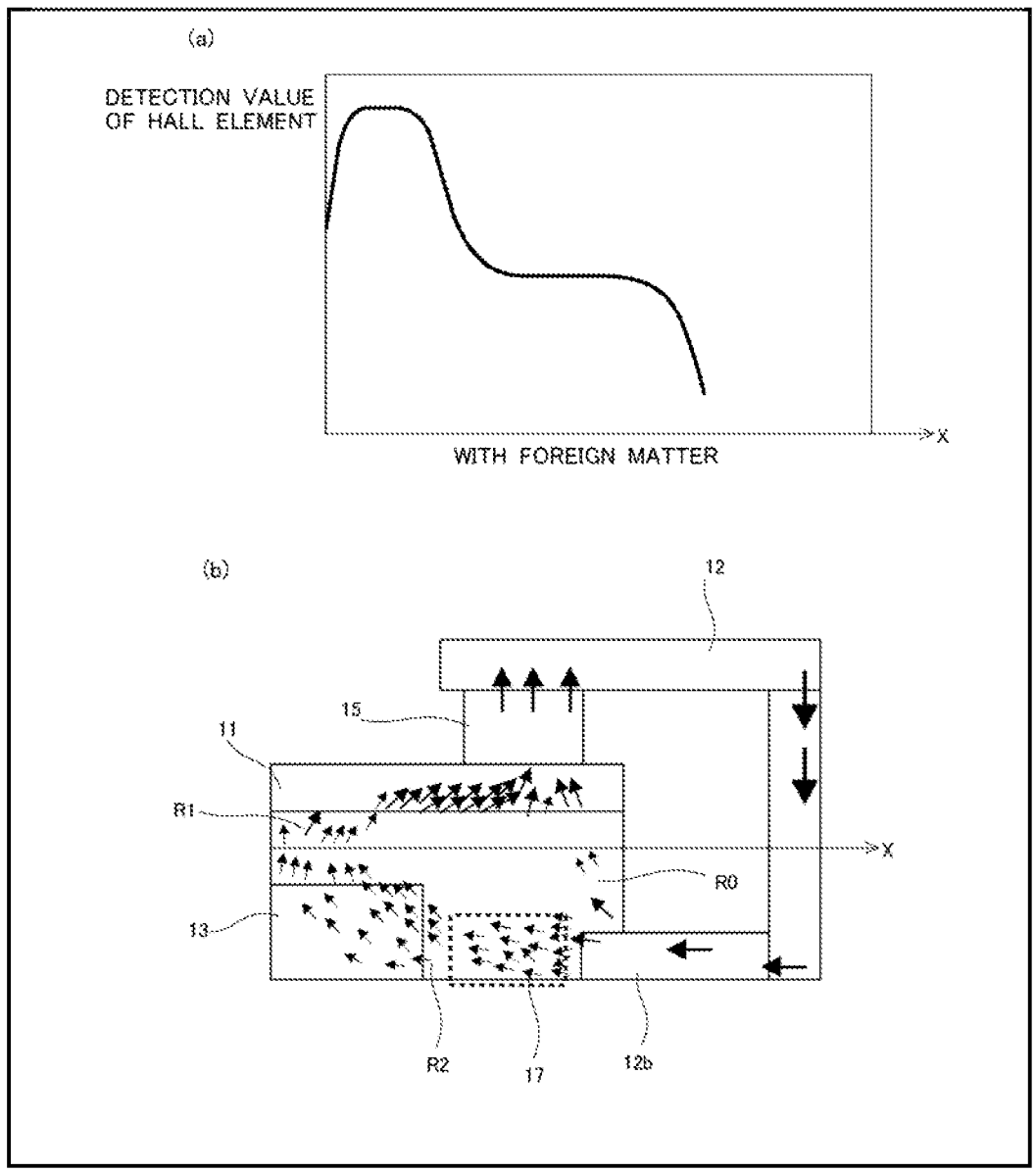
FIG. 6 shows a magnetic flux distribution in the magnetic circuit formed in the foreign matter detecting device when the foreign matter exists in the foreign matter detecting device shown in FIG. 3.

As described above, in relation to the two magnetic circuits formed in the foreign matter detecting device 10, the amount of the magnetic flux flowing through each of the magnetic circuits changes depending on the amount of retention of the foreign matter in the retaining portion 17. In this context, FIGS. 5 and 6 show results of the numerical analysis performed by a computer in relation to the flow of the magnetic flux flowing through the respective yoke portions and the respective spaces when the foreign matter detecting device 10 is constructed by using the permanent magnet 15 having the predetermined magnetic force. The condition (for example, the magnetic force of the permanent magnet 15 and the dimensions of the respective yoke portions) shown in FIG. 5, which relates to the configuration of the foreign matter detecting device 10, is the same as that shown in FIG. 6. FIG. 5 shows the result of the numerical analysis in the state in which the foreign matter is not retained in the retaining portion 17, and FIG. 6 shows the result of the numerical analysis in the state in which the foreign matter is sufficiently retained in the retaining portion 17.

Specifically, the upper part (a) of FIG. 5 shows the transition of the magnetic flux density provided along a predetermined axis X in the state in which the foreign matter is not retained in the retaining portion 17, and the lower part (b) schematically shows the magnetic flux density provided in an assumed model of the foreign matter detecting device (foreign matter detecting device depicted in the same cross section as that of FIG. 3). Note that the predetermined axis X is the virtual line which extends in the relative movement direction of the movable block 2 from an approximately middle position between the first yoke portion 11 and the detour yoke portion 13 in the first detour space R1 toward the second yoke portion 12. Further, as for the magnetic flux density shown in the lower part (b), the direction of the magnetic flux corresponds to the direction of the arrow, and the magnitude of the magnetic flux density corresponds to the size of the arrow. Further, the upper part (a) of FIG. 6 shows the transition of the magnetic flux density provided along the predetermined axis X in the state in which the foreign matter is sufficiently retained in the retaining portion 17, and the lower part (b) schematically shows the magnetic flux density provided in the assumed model of the foreign matter detecting device.

As understood from the comparison between FIGS. 5 and 6, when the foreign matter does not exist in the retaining portion 17, most of the magnetic flux flows toward the reference magnetic circuit S1 including the reference space R0 on account of the presence of the magnetic resistance of the first detour space R1 and the magnetic resistance of the second detour space R2 larger than the magnetic resistance in each of the yoke portions. As a result, the detection value, which is obtained by the Hall element 16 provided in the first detour space R1, is relatively low (see FIG. 5A). On the other hand, when the foreign matter enters the retaining portion 17, and the amount of retention thereof is progressively increased, then the magnetic resistance of the second detour space R2 progressively approaches the magnetic resistance in each of the yoke portions, and hence most of the magnetic flux flows toward the detour magnetic circuit S2 including the first detour space R1. As a result, the detection value, which is obtained by the Hall element 16 provided in the first detour space R1, is larger than that obtained for the case shown in FIG. 5 (see FIG. 6A). As described above, in the foreign matter detecting device 10, the foreign matter is progressively retained in the retaining portion 17, and thus the range of variation of the detection value of the Hall element 16 is increased, for the following reason. That is, the flow of the magnetic flux is greatly switched, if the amount of retention of the foreign matter in the retaining portion 17 is increased to some extent, in accordance with the relationship of the magnetic resistances of the respective spaces represented by Expression 4 described above. As a result, it is possible to highly accurately detect the amount of retention of the foreign matter in the retaining portion 17, i.e., the state of retention of the foreign matter by detecting the change of the magnetic flux density corresponding to the amount of retention of the foreign matter by means of the Hall element 16 provided in the first detour space R1. Further, as described above, in the foreign matter detecting device 10, the large change in the magnetic flux density is obtained in accordance with the amount of retention of the foreign matter. Therefore, it is possible to precisely detect the presence of the foreign matter even when the amount of retention is small.

Further, as shown in FIG. 2, the foreign matter detecting device 10 is attached to the end plate 5 so that the opening portion 17a of the retaining portion 17 of the foreign matter detecting device 10 is not overlapped with the bolt attachment hole 32 provided on the upper surface 33 of the track rail 3 when the movable block 2 relatively moves on the track rail 3, and the opening portion 17a is disposed at the position deviated in the widthwise direction of the track rail 3 from the central axis in the longitudinal direction of the track rail 3. In relation thereto, the following possibility is considered. That is, if the bolt, which is used to fix the track rail 3 in the bolt attachment hole 32, is formed of a magnetic material, the presence of the bolt may disturb the magnetic resistance in the retaining portion 17 in the vicinity of the opening portion 17*a*, i.e., the magnetic resistance of the second detour space R2. As a result, the change in the magnetic flux density irrelevant to the amount of retention of the foreign matter in the retaining portion 17 may be detected by the Hall element 16, and the detection of the foreign matter may be erroneously performed. Therefore, the more accurate detection of the foreign matter is realized by allowing the position of the opening portion 17*a* to be the position deviated from the bolt attachment hole 32 as described above.

Further, the detection signal of the foreign matter, which is outputted from the foreign matter detecting device 10, may be a detection signal corresponding to the amount of retention of the foreign matter in the retaining portion 17. In another method, it is also allowable to use a signal which means whether or not the foreign matter, which is in an amount of not less than a predetermined retention amount, is retained in the retaining portion 17, by making comparison with a reference value corresponding to the predetermined retention amount. Further, the detection signal may be transmitted in a wireless manner from the foreign matter detecting device 10 to an external apparatus, or the detection signal may be transmitted in a wired manner. The user can make the judgment in relation to the maintenance of the linear guide 1 on the basis of the detection signal transmitted from the foreign matter detecting device 10. If the maintenance is performed for the linear guide 1 on the basis of the detection signal, the foreign matter detecting device 10 can be utilized again by washing away the foreign matter retained in the retaining portion 17 by means of the washing in conformity with the maintenance.

Modified Embodiment

In the embodiment described above, the Hall element is arranged in the first detour space R1. However, in place of such a form or mode, the Hall element may be arranged in the reference space R0. As shown in FIGS. 5 and 6, when the amount of retention of the foreign matter is progressively increased in the retaining portion 17, the switching thereby occurs in the flow of the magnetic flux from the reference magnetic circuit S1 to the detour magnetic circuit S2. Therefore, the change in the magnetic flux density is also relatively increased in the reference space R0. That is, when the amount of retention of the foreign matter is increased, the magnetic flux density in the reference space R0 is greatly changed from the state in which the magnetic flux density is relatively large to the state in which the magnetic flux density is small. The large decrease in the magnetic flux density is detected by the Hall element 16. Accordingly, in the same manner as in the embodiment described above, it is possible to highly accurately detect the amount of retention of the foreign matter in the retaining portion 17, i.e., the state of retention of the foreign matter. Further, it is possible to precisely detect the presence of the foreign matter even when the amount of retention is small. In still another method, it is also allowable that Hall elements are arranged in both of the first detour space R1 and the second detour space R2, and the state of retention of the foreign matter is detected in the retaining portion 17 by utilizing the change in the magnetic flux density in the both spaces.

DESCRIPTION OF THE REFERENCE SIGNS

1: linear guide, 2: movable block, 3: track rail, 4: main block body, 5: end plate, 10: foreign matter detecting device, 10*a*: device body, 11: first yoke portion, 12: second yoke portion, 12*b*: end portion, 13: detour yoke portion, 15: permanent magnet, 16: Hall element, 17: retaining portion, 17*a*: opening portion, 17*b*: intake groove, 31: ball rolling surface, 32: bolt attachment hole, 33: upper surface, 41: attachment surface, 41*a*, 41*b*: end portion, R0: reference space, R1: first detour space, R2: second detour space.

The invention claimed is:

1. A foreign matter detecting device, for detecting a predetermined foreign matter including a magnetic material, the foreign matter detecting device comprising:
   a permanent magnet;
   a first yoke portion which is arranged while adjoining the permanent magnet;
   a second yoke portion which adjoins the permanent magnet at a region different from that of the first yoke portion, the second yoke portion being arranged separately at a second yoke predetermined region different from the adjoining region while interposing a predetermined reference space with respect to the first yoke portion;
   a detour yoke portion which is arranged separately while interposing a first detour space different from the predetermined reference space, with respect to the first yoke portion and which is arranged separately while interposing a second detour space with respect to the second yoke predetermined region of the second yoke portion, a magnetic resistance of the first detour space being smaller than a magnetic resistance of the predetermined reference space, and the sum of magnetic resistances of the second detour space and the first detour space being larger than the magnetic resistance of the predetermined reference space;
   a retaining portion which is provided so that the predetermined foreign matter can enter the retaining portion via an opening portion provided on an outer surface of a device body and the entered predetermined foreign matter is retained in the second detour space; and
   a detecting portion configured to output a detection signal in relation to the predetermined foreign matter on the basis of a magnetic flux density provided in at least any one of spaces of the predetermined reference space and the first detour space, corresponding to an amount of retention of the predetermined foreign matter in the retaining portion.

2. The foreign matter detecting device according to claim 1, wherein:
   the detecting portion has a sensor element which is capable of detecting the magnetic flux density in the first detour space;
   the magnetic flux density in the first detour space is increased if the amount of retention of the predetermined foreign matter retained in the retaining portion becomes large, as compared with if the amount of retention is small; and
   the detecting portion outputs the detection signal on the basis of the magnetic flux density which is provided in the first detour space and which is detected by the sensor element.

3. The foreign matter detecting device according to claim 1, wherein:
   the detecting portion has a sensor element which is capable of detecting the magnetic flux density in the predetermined reference space;
   the magnetic flux density in the predetermined reference space is lowered if the amount of retention of the predetermined foreign matter retained in the retaining portion becomes large, as compared with if the amount of retention is small; and the detecting portion outputs the detection signal on the basis of the magnetic flux density which is provided in the predetermined reference space and which is detected by the sensor element.

4. The foreign matter detecting device according to claim 1, wherein the predetermined foreign matter, which has entered the retaining portion, is retained in the retaining portion by means of a magnetic force of the permanent magnet.

5. A linear guide comprising:
the foreign matter detecting device as defined in claim 1;
a track member which extends in a longitudinal direction; and
a movable member which is arranged opposingly to the track member with a plurality of rolling members intervening therebetween and which is relatively movable in the longitudinal direction of the track member, wherein:

the foreign matter detecting device is provided at a predetermined end portion in a relative movement direction of the movable member so that the opening portion is open while being opposed to the track member.

6. The linear guide according to claim 5, wherein an intake groove, which extends in the relative movement direction of the movable member and which is linked to the opening portion, is provided on the outer surface of the device body of the foreign matter detecting device.

7. The linear guide according to claim 5, wherein:
the track member has an attachment hole for attaching the track member to a predetermined fixed member on an opposing surface on which the movable member is opposed to the track member and the plurality of rolling members do not roll; and
the foreign matter detecting device is provided at the predetermined end portion of the movable member so that the opening portion does not overlap the attachment hole when the movable member relatively moves with respect to the track member.

* * * * *